United States Patent [19]

Brinkerhoff et al.

[11] Patent Number: 5,222,963
[45] Date of Patent: Jun. 29, 1993

[54] PULL-THROUGH CIRCULAR ANASTOMOSIC INTRALUMINAL STAPLER WITH ABSORBABLE FASTENER MEANS

[75] Inventors: Ronald J. Brinkerhoff, Amelia; Mark S. Zeiner; Michael B. Miller, both of Cincinnati, all of Ohio; James A. Transue, Bridgewater, N.J.

[73] Assignee: Ethicon, Inc., Somerville, N.J.

[21] Appl. No.: 642,496

[22] Filed: Jan. 17, 1991

[51] Int. Cl.⁵ ............................................. A61B 17/00
[52] U.S. Cl. ...................................... 606/153; 606/154; 606/220; 227/179; 24/616; 411/457; 411/509; 411/512
[58] Field of Search .................. 606/153, 154, 220; 227/175-180, 19; 411/457, 509, 512; 24/616, 615, 590, 548, 621, 295, 297

[56] References Cited

U.S. PATENT DOCUMENTS

| | | | |
|---|---|---|---|
| 2,638,901 | 5/1953 | Sugarbaker | 606/153 |
| 4,198,982 | 4/1980 | Fortner et al. | 227/180 |
| 4,294,255 | 10/1981 | Geroc | 606/153 |
| 4,476,863 | 10/1984 | Kanshin et al. | 128/305 |
| 4,523,592 | 6/1985 | Daniel | 606/153 |
| 4,589,416 | 5/1986 | Green | 606/220 |
| 4,610,250 | 9/1986 | Green | 606/220 |
| 4,805,617 | 2/1989 | Bedi et al. | 606/220 |
| 4,873,977 | 10/1989 | Avant et al. | 604/96 |
| 4,917,114 | 4/1990 | Green et al. | 227/179 |
| 4,957,499 | 9/1990 | Lipatov et al. | 606/153 |

FOREIGN PATENT DOCUMENTS 070923 2/1983 European Pat. Off.
335552 10/1989 European Pat. Off.

Primary Examiner—Stephen C. Pellegrino
Assistant Examiner—Gary Jackson
Attorney, Agent, or Firm—Paul A. Coletti

[57] ABSTRACT

A mechanism which is capable of anastomosis of two lumens by an absorbable fastener. The fastener is made from two washer-like plates. One such plate has holes to receive latching prongs protruding from the other plate. Fastening is done through a single linear motion that causes the prongs to pierce the tissue, latches the prongs into a receiver and causes a knife blade to cut through excess fastener material and tissue. The ease of removal, by pulling the mechanism thorugh the formed anastomosis, is greatly enhanced. The system can be used such that the plates can be placed in any configuration to properly anastomose tissue.

30 Claims, 8 Drawing Sheets

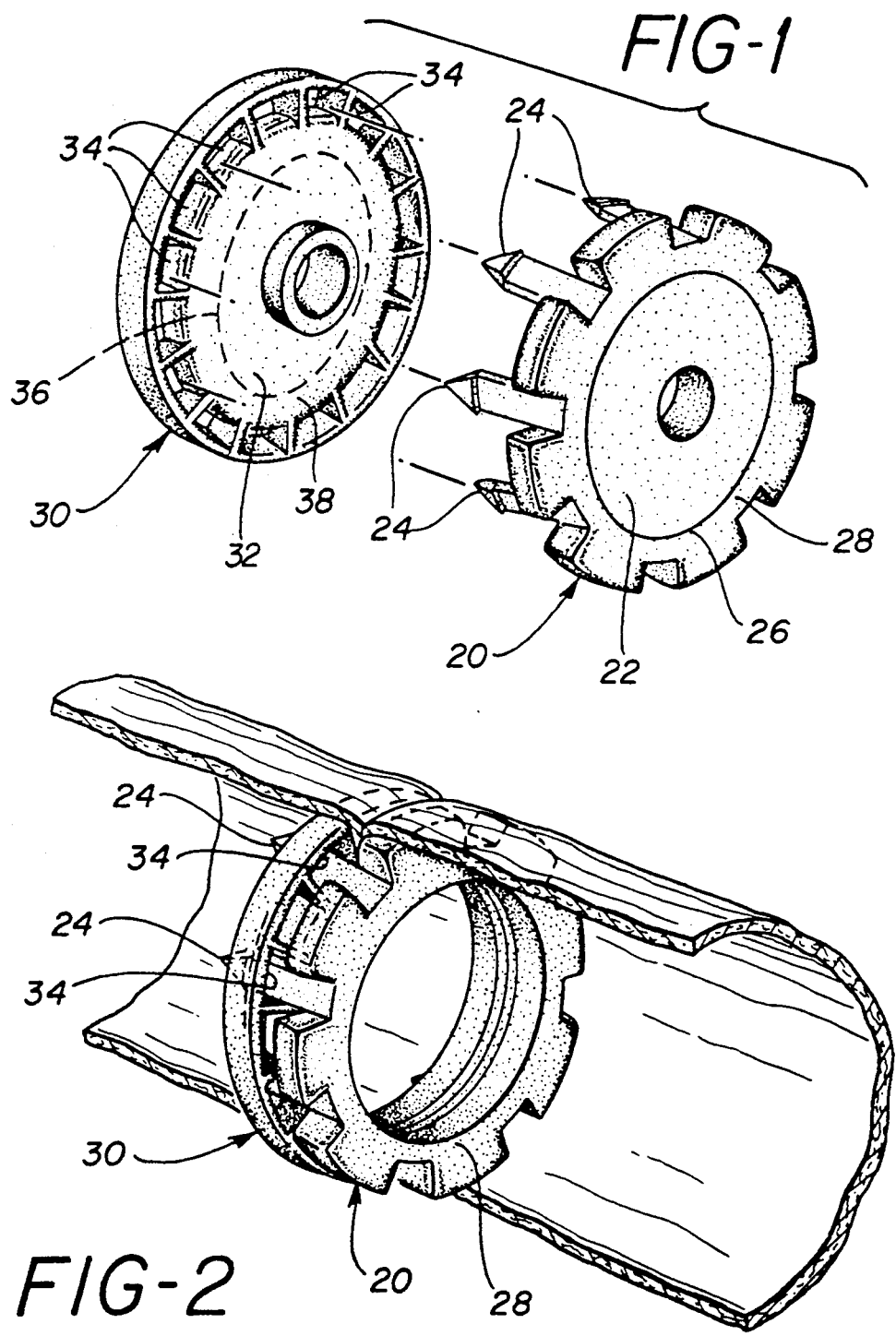

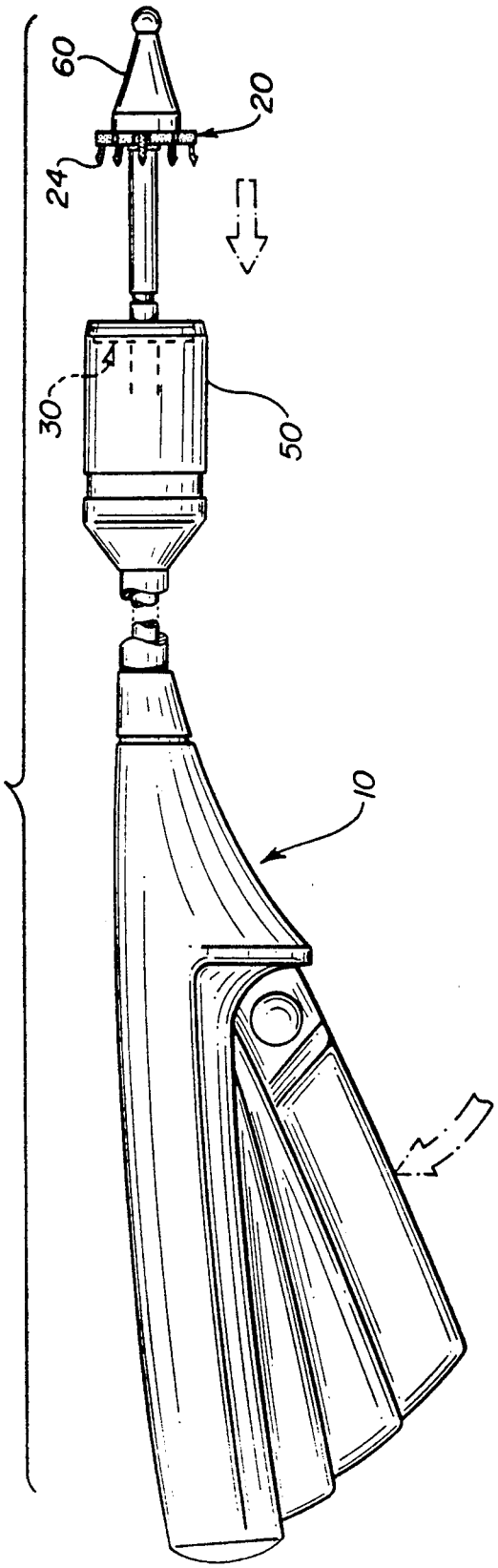
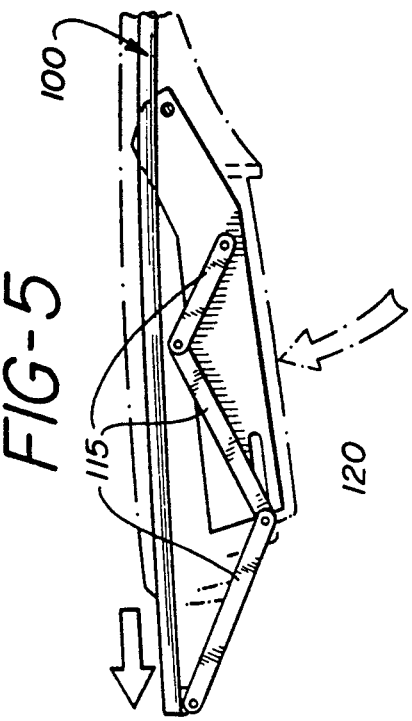
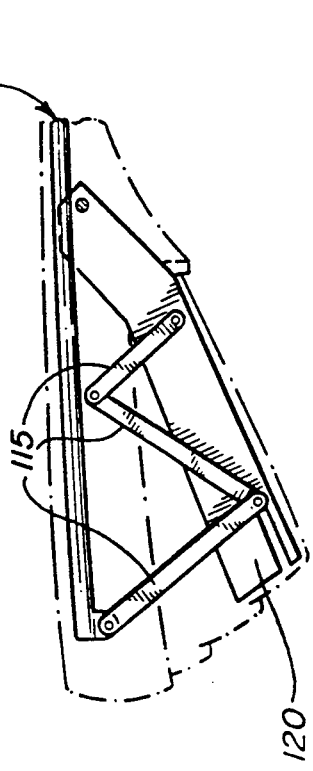

PULL-THROUGH CIRCULAR ANASTOMOSIC INTRALUMINAL STAPLER WITH ABSORBABLE FASTENER MEANS

FIELD OF THE INVENTION

Generally, this invention relates to an apparatus for circular surgical stapling. More specifically, this invention relates to anastomotic fastening using absorbable staples. Most specifically, this invention relates to circular anastomotic fastening using absorbable staples, and the means to apply such staples.

BACKGROUND OF THE INVENTION

Currently, there exist a number of surgical anastomotic circular staplers. Generally, these staplers are used to connect severed lumen with a circular ring of staples displayed around a circumference to connect the tissue. In most instances, a knife mechanism is used to cut the tissue within the circumference of the staple ring. The ring of staples is generally a number of small metallic surgical staples, usually between 20 and 40 staples, which form a ring roughly 2 cm to 4 cm in diameter. Naturally, with the circular staples there must be minimum constriction of the tissue after healing, and the lumen must be maintained as near as possible as prior to the procedure, to allow normal passage of fluids.

With this type of stapler, there must be a complete 360° seal of tissue so that no gaps exist between the connected tissue. In addition, it is naturally desirable that when the tissue is connected, the volume within which the tissue is cut be maintained so that the tissue is continually able to pass fluids without encountering constricting tissue.

In addition, with such circular anastomotic staplers it is desirable to make staplers which are disposable. That is, disposable staplers are now well accepted by surgeons. Disposable surgical staplers also help prevent the spreading of bacteria or germs. Naturally, the surgeon also desires a manual stapler which gives good off-the-shelf reliability and allows a controlled one-handed operation.

Most importantly, there has been a need for absorbable staplers in the circular fastening market. This is due in part to the prior incapacity to produce a circular anastomotic stapling mechanism where the staples are able to be received within receivers and adequate forces can be generated to hold the tissue together and to clamp the staples. In addition, it is critical in this system to maintain tolerances which enable alignment of staples or fasteners within the receivers. To accomplish this in an absorbable circular anastomotic stapler would increase the likelihood of use of such a stapler within hard to reach or marginally compliant lumen. It is to be realized that typical absorbable fasteners have an enlarged size, preventing use in such places.

Furthermore, it is desirable to replace a standard staple line with two adaptively connectable fasteners. In this way, the need for bending of staples is removed, and yet closure and hemostasis are possible. Of course, by attempting to formulate a system in which a standard staple line is replaced, it would be desirable to formulate such a stapler so that the stapler itself can be pulled through the attached part of the tissue without the need for removing the anvil portion of the stapler. This results in a rapid and efficient method of removing the stapler. In the desire for creating such a adaptively connectable mating fastener, it is naturally desirable that these fasteners are both Positively aligned and latching, and that they are formulated so that the instrument creates closure at some constantly adjustable closure pressure. If the pressure required to attach the latching members together remains constant, it is much easier to close and latch the instrument with a smooth, efficient single stroke. Alternately, it may be desirable to rely on the constant closure pressure to attach the fastener through the tissue, and then, in a separate action, actually close the tissue with the instrument.

In such a system it would also be desirable to readily see whether the fasteners are connected and the tissue is adequately closed. This is especially true where the instrument is pulled through the connected tissue. Also, these type connections should be available on all circular-type instruments, including those with curved shafts or instruments containing trocars or flexible shafts.

SUMMARY OF THE INVENTION

It is therefore an object of this invention to provide a circular anastomotic stapler which provides good alignment between staples and receivers. It is further an object of the invention to provide an absorbable circular anastomotic stapler which provides such alignment.

It is yet another object of the invention to provide a means which apply such absorbable staples, and yet maintain alignment between staple and receiver.

It is further desirable to create a surgical anastomotic stapler which accomplishes these criteria while allowing the user to cut and remove inner portions of tissue and or staple which constrict the volume of fluid which passes through the connected lumen.

It is again desirable to provide such a circular anastomotic stapler wherein the standard staple line are replaced by two separably connectable fastening parts.

It may yet be more desirable that the separatly connectable parts have a separable center which will result in the pulling through of the device after the fasteners are connected.

While it may desirable in some instances to form the fasteners of the invention from absorbable means, it is again more desirable that the mechanism formed has fasteners which are both latching and self-aligning.

It is further desirable that the closure is affected either with a single or double stroke, but at some predetermined closure dimension.

It is further desirable that the instrument be capable of providing quick, ready, and accurate user feedback in that the remaining fastened tissue is easily inspectable for closure and hemostasis while the remainder of the instrument can be removed rapidly from the site.

It is yet again desirable to be able to perform such a stapling operation with a stapler that may be pulled through the resulting anastomosed tissue.

It is finally desirable that such an instrument be capable of being used with either a straight or curved shaft instrument, with or without a trocar attached to the head portion of the shaft.

These and other objects of the invention are accomplished in a mechanism arranged to anastomose two lumens with an absorbable fastener. The fastener is created from two washer-like pieces. One of the washer-like pieces has holes which are adaptable to receive latching prongs protruding from the other such washer-like piece. Fastening is accomplished through a singluar linear motion in which the prongs pierce the tissue, then latch within the holes in the receiver. Finally, the tissue is cut by a circular knife which also creates a final ring-like shape of the fastener within the tissue. The inner portion of each of the washer-like pieces is removed along with the cut tissue when the instrument is removed from the lumen.

The knife is able to shear the tissue against a die when the knife overcomes a spring force after latching and causes the knife to cut both tissue and the inner portion of each of the washer-like pieces. Overstroke of the die or the knife causes releasing closure from the distal end of the instruments so that removal is easy. One such mechanism is able to reverse the position of receivers and flanges so that the fastener prongs can be oriented in any direction before use.

DETAILED DESCRIPTION OF THE DRAWINGS

The invention will be better understood by the attached drawings in which:

FIG. 1 and FIG. 11 are perspective views of a fastener and receiver of the invention, of which

FIG. 2 is a perspective view of the components of FIG. 1 joined inside lumen;

FIG. 3 is a side elevation of a means for applying the fasteners in FIG. 1;

Figure 6:
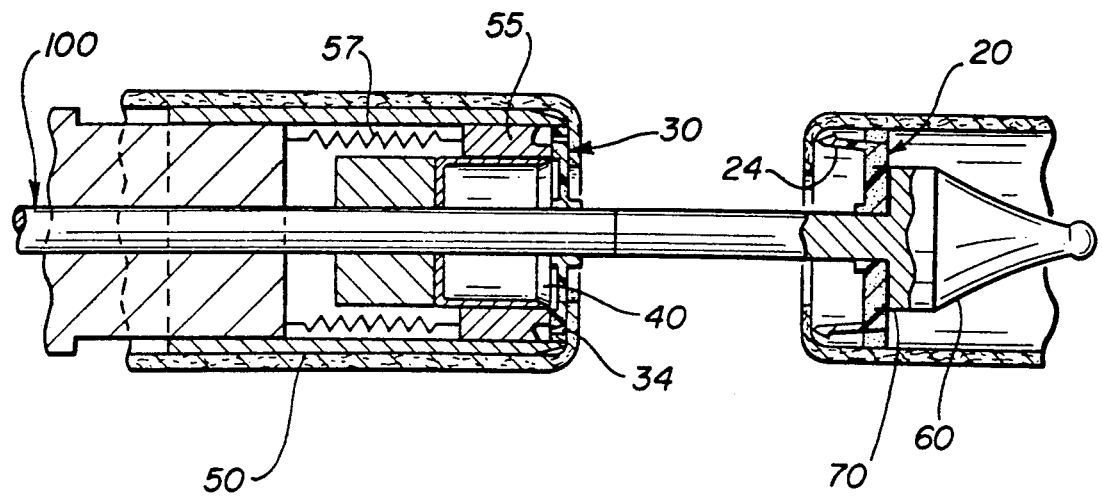
Figure 7:
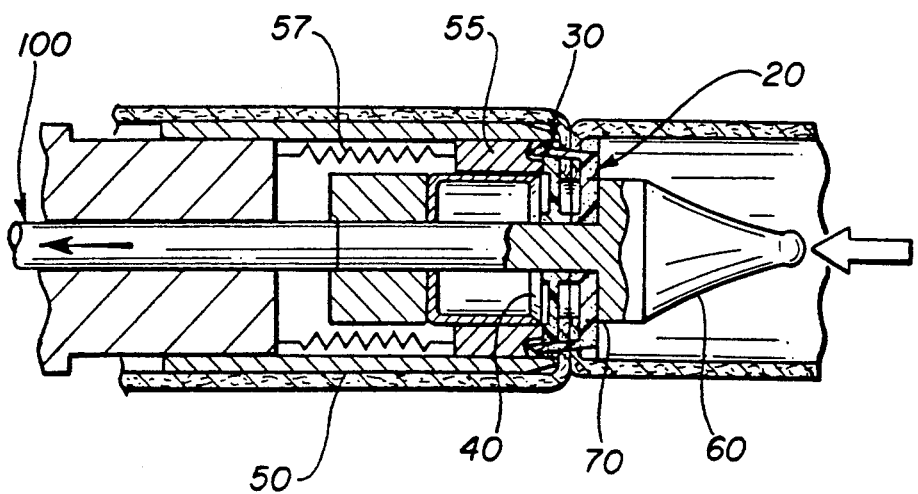
Figure 8:
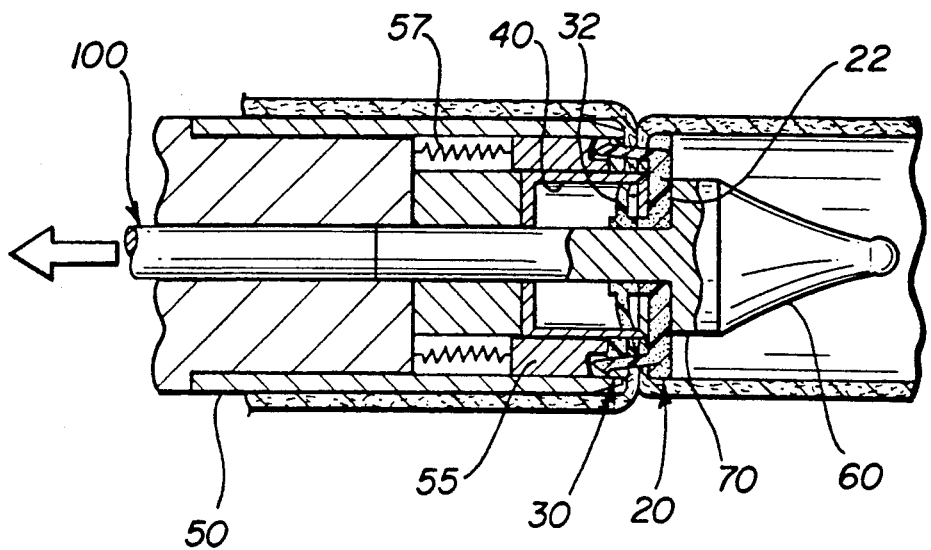
Figure 9:
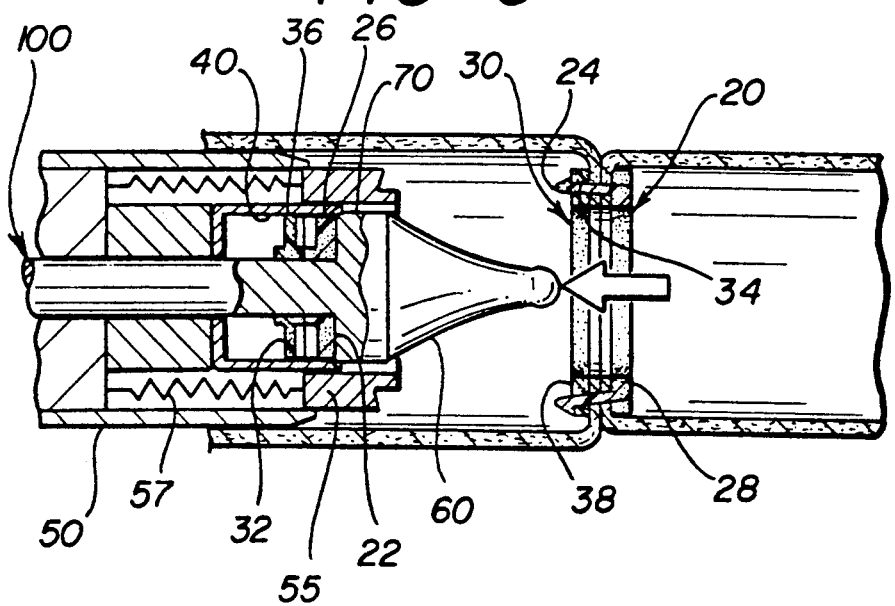
Figure 10:
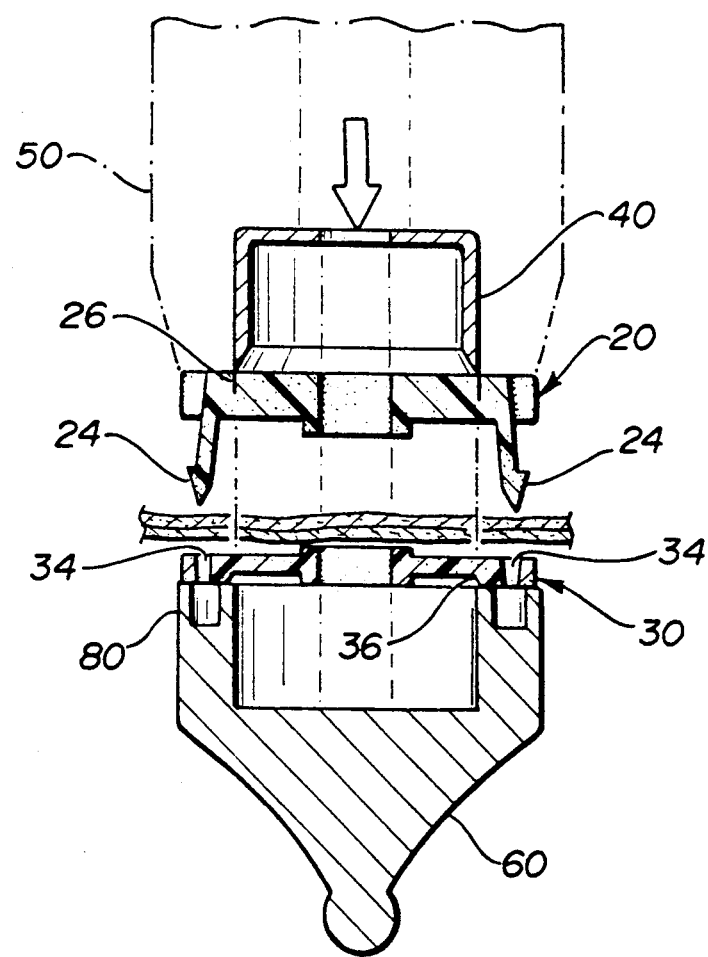
Figure 13:
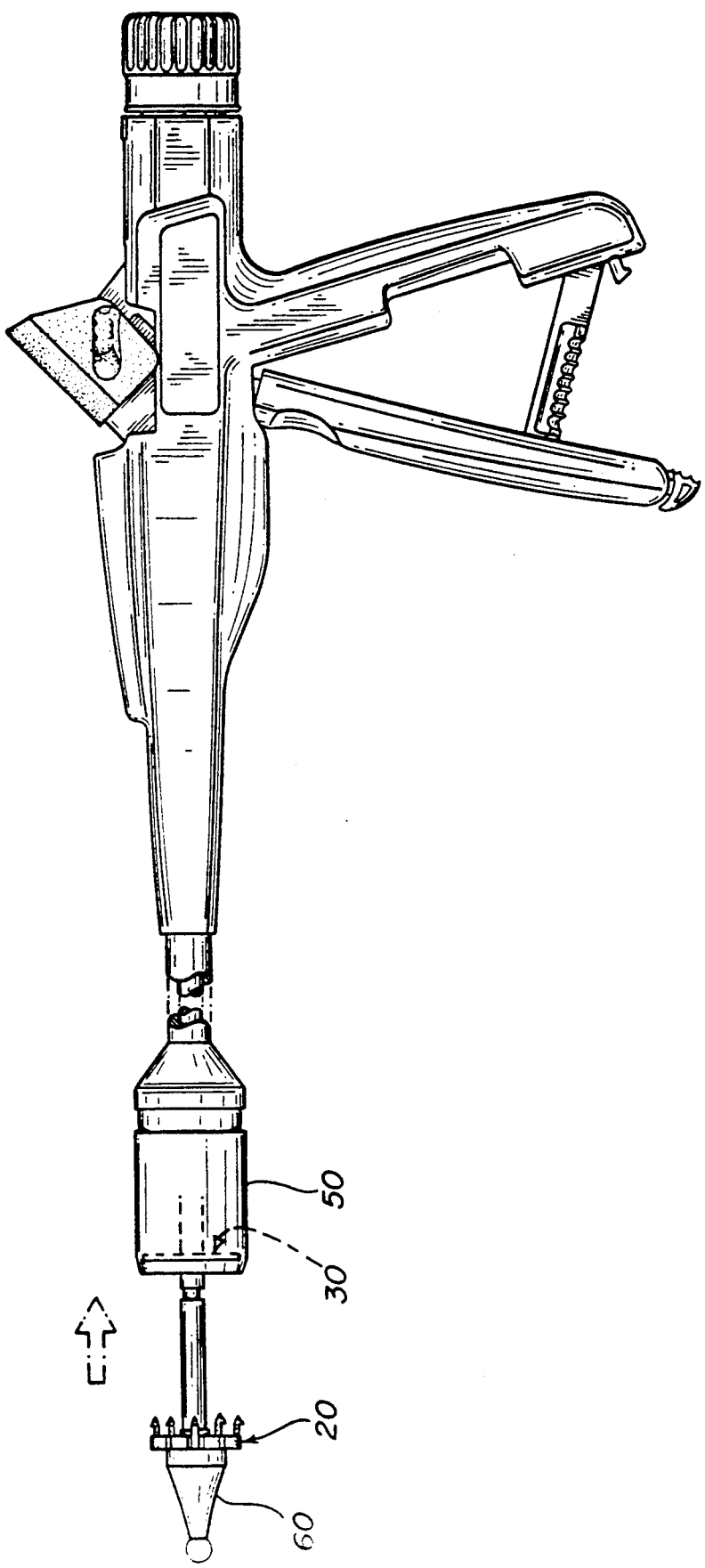
Figure 14:
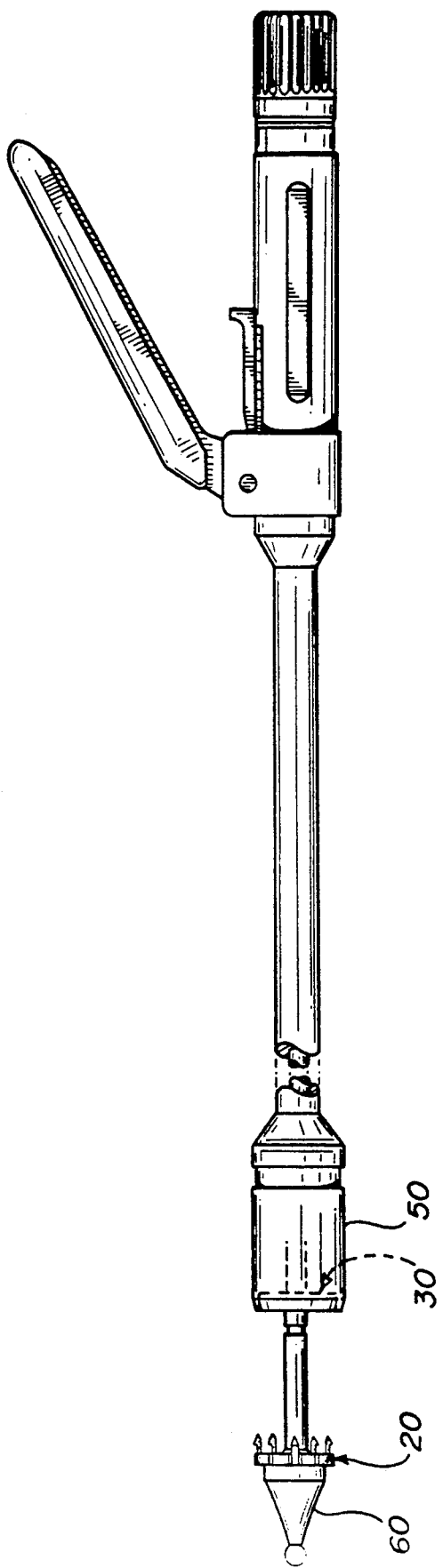

FIGS. 4 and 5 demonstrate a handle mechanism of the means of FIG. 3;

FIGS. 10, 13 and 14 are is an alternate embodiments of the means of FIG. 3, in cross-section; and FIGS. 6, 7, 8 and 9 are particularized cross-sectional views of the application of the means in FIG. 1 as used in the apparatus of FIG. 3.

DETAILED DESCRIPTION OF THE INVENTION

As seen in FIGS. 1 through 12, there is disclosed a surgical stapling device which is capable of performing surgical anastomotic circular stapling. As seen in FIG. 3, this stapler 10 is capable of holding the fasteners or plates 20, 30 as indicated in FIG. 1.

As seen in FIGS. 1 and 2, 11 and 12 these fasteners 20, 30 are generally absorbable and formed from known biocompatible materials. Of course, it is to be realized that the material may also be metallic without departing from this invention. These fasteners 20, 30 replace a standard anastomotic staple line. Each of these fasteners is plate shaped and at least one such fastener contains a central toric section 22, 32 to be removed from the plates 20, 30. This toric section allows the pull-through function of the fastener system. Also, one of the fasteners 20 has prongs 24 which are sharpened so as to pierce tissue. The other fastener 30 has multiple receivers 34 which number more than the prongs 24 on plate 20. This arrangement allows each of the prongs 24 to have little or no difficulty in alignment within the receivers 34 on the other fastener 30. Nonetheless, each plate 20, 30 generally has at least eight such prongs and receivers 24, 34.

Figure 11:
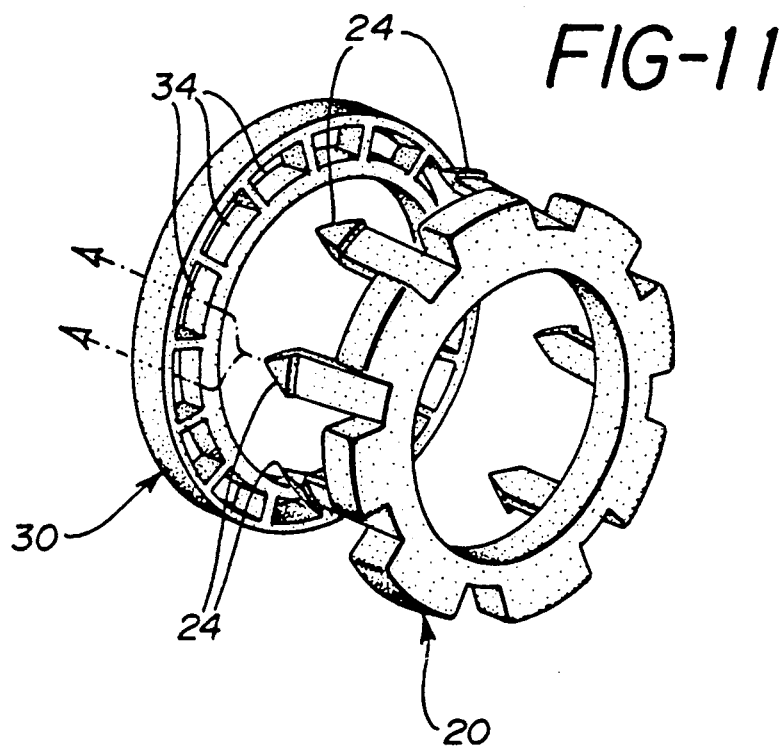
Figure 12:
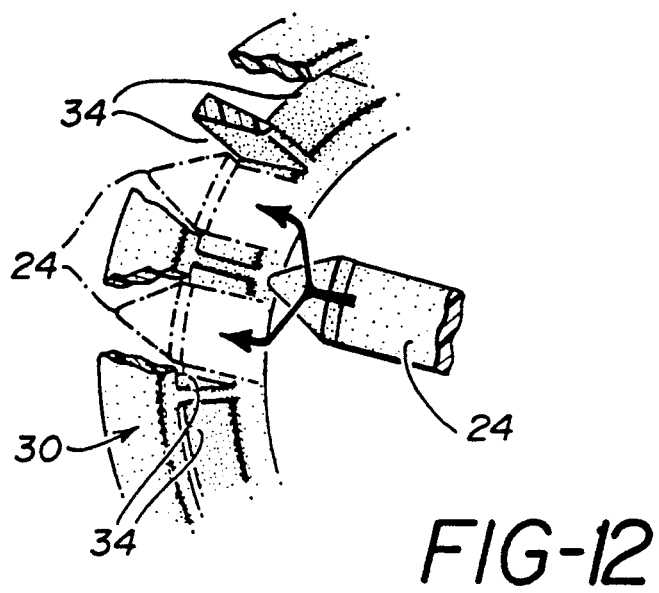
FIG. 12 is a perspective view partially cut-away.

The alignment aspect is very important concerning these fasteners 20, 30. It is to be realized that with conventional staples, and conventional staplers, the staples are pre-aligned with anvils so that the staples are readily formed after piercing through tissue. In contrast, it is necessary to have these fasteners 20, 30 self-aligning so that the fasteners themselves meet with one another. Thus, the prongs 24 are configured so that they will readily be urged into each of the receiving receivers 34. For instance, as seen in FIGS. 11 and 12, there are displayed twice as many prongs 24 as there are receivers 34, so that alignment requires very little rotation of fastener 20. The receivers 34 are equal or greater in number to the prongs 24 and are wide enough so that the prongs 24 will fit within each of the receivers 34. Also, either fastener is capable of rotating slightly within the head or anvil portion in which it is held so that this alignment may take place. This will become more readily understandable when the stapler 10 is further explained in a later portion of this specification.

The plates 20, 30 are formed to be generally thin (about 0.010" to 0.030" thick) so that they do not take up much space within the housing of an instrument or between tissue; as well, with thinner plates 20, 30 the force required to fire a plate 20, 30 is reduced, resulting in easier surgeon use. Naturally, such reduced thickness is configured so as to not inhibit holding strength of the fasteners 20, 30.

It will be noticed from the FIGS. 1 and 2 that each plate 20, 30 has a frangible ring 26, 36 within the circumference of the plate. These rings 26, 36 are intended to be broken by the force of a knife 40 (best seen in FIG. 6) so that fasteners 20, 30 are broken and the frangible rings 26, 36 of each of the plates 20, 30 is pulled within the head 50 of instrument 10. Stapler 10 is then removed from the cutting site, leaving the outer portions 23, 38 of plates 20, 30 locked and connected with connected tissue placed between.

The fasteners 20, 30 have been formed either without a center or with separable rings 26, 36 center so that the rings 26, 36 as well as the cut tissue is gathered within the head 50 of the instrument 10. This allows the pulling through of the anvil 60 of the instrument 40, as is best seen in FIG. 9. Previously, it would be necessary to detach the anvil 60 from the staple before pulling the instrument through the connected tissue. This capability of not "unbuttoning" the anvil 60 from the stapler 10 results in a vast improvement compared to some previous circular anastomotic staplers.

The instrument 10 in which these plates 20, 30 are used is seen in FIG. 3. Stapler 10 is a stapler with a generally circular cross-section of the the type normally used for anastomosis. However, as better seen in FIGS. 6, 7, 8 and 9, this stapler 10 contains a pair of plates 20, 30 seated within the stapling area. One plate 20, 30 is placed within the anvil section 60 and one within the head or driving section 50. The instrument 10 itself performs the anastomosis by attaching plates 20, 30 rather than conventional staples.

As better seen in the operational breakdown in FIGS. 6, 7, 8 and 9, first, tissue held around the head 50 is approximated to tissue held on the anvil 60 so that the tissue is ready for anastomosis. Next, the prongs 24 of one of the fasteners 20 pierce both layers of tissue and lock within the receivers 34 of the other fastener 30.

After locking, a knife 40 in the instrument is pushed forward by further compression of the handle mechanism 100. First one plate 20 is cut, then tissue (both layers), then the last plate 30. Thus, as in FIG. 9, as held within the anvil 60, there is formed a package containing inner broken frangible rings 26, 36 and central toric sections 22, 32 holding the cut tissue. The fasteners 20, 30 remaining as the outer portions 28, 38 are locked together with tissue held between. At that point, the instrument 10 is able to be removed by pulling it through the tissue that has been cut and away from the area which has been anastomosed.

As better seen in FIGS. 4, 5, 6 and 10, the instrument may take on a number of different configurations. First, as better seen in FIG. 6, the mechanism may be formed with a male die 70 held within the anvil 60 of the instrument 10. In this manner the anvil 60 will be pulled into the instrument. As seen in the mechanism of FIGS. 4 and 5, the handle 100 causes reversal of motion in the direction of the arrow, so that the anvil 60 is pulled toward the handle. This creates a force from anvil 60 on plate 20. The plate 20 receives the force exerted against it and the inner frangible ring 26 of the plate 22 breaks at the frangible ring 26, leaving the outer portion 28.

This is accomplished, of course, after the prongs 24 of the plate 20 have pierced tissue and been received within the receivers 34 end of the plate 30, enclosed within the fastening block 55 on the head 50 of the instrument 10. The fastening block 55 is held forward by a timing spring 57. This timing spring 57 has adequate force to cause the tissue to be pierced by prongs 24 and the receivers 34 to be locked onto plate 20, so that the tissue is adequately held between both plates 20, 30.

It is to be noted that timing spring 57 is therefore capable of providing a constant closure pressure throughout the closure and cutting of the tissue. This enables the designer to easily adapt stapler 10 to create enough mechanical advantage so that closure and latching as well as cutting can be accomplished in a single stroke of the mechanism. Or, it may be desirable to first pierce the tissue and latch with one stroke of the mechanism. Then, it may be further desirable to complete closure and cut the tissue with a second stroke. This may result in further reliability and ease of firing of the mechanism.

The force from the anvil 60 then overcomes the tissue as well as plates 20, 30 and spring 57 force so that the plate 30 abuts knife 40. First, knife 40 cuts through the frangible ring 36, then the two layers of tissue. Frangible ring 26 of plate 20 is then either cut by the knife 40, or broken by the anvil 60, depending upon design specifications.

What remains therefore is for the entire anvil 60 with tissue and plates 20, 30 held therein to be pulled toward the knife 40 so that a volume is held within the handle head 50. This is then pulled away from the connected tissue. Thus, the remaining outer portions 28, 38 with tissue held therein and locked against the anvil are held so that a properly anastomosed lumen is created.

On the other hand, as seen in FIG. 10, there is also possible the reversal of the plates 20, 30 so that the pronged plate 20 is on the head portion 50 of the instrument 10. In this way, force is created in the direction of the arrow by the knife 40 to push against the plate 20. Plate 20 then pierces both layers of tissue.

The tissue is then locked within the upper receiving plate 30 which contains receivers 34 and a female die 80. After locking, knife 40 is advanced further so that it breaks first the pronged plate 20 at frangible ring 28, then the two layers of tissue, then the lower plate 30 at frangible ring 36. Thus, the entire cut portion of tissue is held within the anvil 60. Anvil is then removed back through the head portion 50 so that properly anastomosed tissued is revealed.

Further examining the mechanism as in FIGS. 3, 4 and 5, it is to be noted that the combination mechanical elements comprising links 115 and slide 120 causes the handle 100 to move forward the knife 40 contained in head 50 of the instrument 10. If one additional link 115 is added, it will be appreciated that the position and motion of knife 40 may be reversed so that the knife 40 retracts into the stapler 110. In this way, it is possible to perform anastomosis with whichever is the desired configuration of the two plates 20, 30.

Of course, it should be noted that the configuration of the plates may be slightly different. For instance, it may be desired to reduce the force necessary to cut through the tissue by removing one of the inner portions 22, 32 of the two plates beforehand. In this way, closure takes place on the outer rings 22, 32 and the knife mechanism 40 abuts only tissue. It can further be envisioned to use a ring-type mechanism where the inner portions 28, 38 of plates 20, 30 do not even exist and only prongs 24 and receivers 34 create closure. Of course knife action should then take place using alternate methods. In this manner, it is possible to reduce force to fire the instrument 10, while maintaining the proper orientation of the rings containing components 24, 34. The only certain requirements, therefore, in any of these embodiments are alignment of the fasteners, the creation of enough force to hold the plates 20, 30, and proper cutting by knife 40 in preparing the anastomosis.

Thus, after the stapler 10 with anvil 60 attached, and cut tissue between, has been pulled through the closed tissue, this results in more accurate and positive user feedback. The user is able to inspect the "donut" of tissue and fastener remaining in the stapler 10. Also, because the instrument has been pulled through the closed tissue, the user is able to inspect the portion of tissue which remains without the instrument obscuring the results obtained by closure. This creates a more reliable and accurate closure system.

Alternately, of course, there is possible the incorporation of the stapling configuration of the present invention in current stapling. As seen in FIGS. 13 and 14, currently produced staplers 100, 200 may be incorporated with the head 50 of this invention, and also may be provided with fasteners 20, 30. Thus, the invention is relatively inexpensive to incorporate into current usage.

These and other embodiments of the invention have been described as above. Of course, it may be possible to vary the stapler and fastener of the present invention without deviating from the intent of this invention. For instance, it is possible to create an apparatus with a curved longitudinal shaft, or having a flexible shaft, or where the shaft portion near the distal end contains a trocar instrument. What is to be realized is that it is the following claims and their equivalents which are meant to cover the scope of the invention.

What is claimed is:

1. An absorbable anastomotic tissue fastener comprising:
    (a) a tissue piercing plate containing a plurality of tissue piercing prongs for insertion through tissue; and
    (b) a receiving plate containing a plurality of receptors capable of locking said prongs therein;
    wherein said tissue is held between said piercing plate and said receiving plate by being maintained on said prongs locked within said receptors and wherein said plates are circular in shape, and said prongs and receptors are positioned on the circumference of said plates and such that said plates are frangible inside said circumferences, such that upon breaking said piercing plate, said prongs contained on a ring on said circumference, and such that upon breaking said receiving plate, said receptors are contained on a ring on said circumference.

2. The fastener of claim 1 wherein said plates are absorbable by the human body.

3. The fastener of claim 1 where said prongs are sharpened to readily pierce tissue.

4. The fastener of claim 3 wherein said prongs contain detent means and said receptors contain latch means such that said detent means locks on said latch means.

5. The fastener of claim 1 wherein said plates are generally flat.

6. The fastener of claim 1 wherein each of said plates are frangible along a weakened portion of said plate, each said weakened portion comprising a ring of reduced thickness located on said plate and capable of breaking upon the exertion of a shear force on said plate.

7. An instrument for anastomotic tissue fastening comprising:
   an anvil capable of holding a first absorbable staple ring;
   a driving mechanism capable of holding a second absorbable staple ring which mates and locks with said first absorbable staple ring, said driving mechanism capable of placing said rings into proximity of each other;
   knife means for cutting tissue, said knife means held within said driving mechanism; and
   first and second absorbable staple rings, wherein one of said absorbable staple rings contains a plurality of tissue piercing prongs arranged circumferentially about said ring for insertion through tissue and the other of said absorbable staple rings contains a plurality of receptors capable of locking said prongs therein with tissue placed between said rings on said prongs, said receptor shaped to engage said prongs so that each said prong is separated by at least a portion of a said receptor, and wherein said knife means are capable of cutting excess tissue contained inside the circumferences of said absorbable staple rings and being pulled through the joined staple rings, and wherein said prongs contain detent means and said receptors contain locking means for locking said receptors when said driving means bring said rings into proximity of each other and wherein said rings are frangible inside their respective circumferences, such that upon said knife means cutting tissue said knife means similarly breaks said rings, such that said prongs are contained on a ring on said circumference, and such that upon breaking said receiving ring said receptors are contained on a ring on said circumference.

8. The instrument of claim 7 wherein said anvil further contains a die into which said knife means are actuable, said knife means exerting a shear force on said tissue against said die.

9. The instrument of claim 8 wherein said die is a female die and said knife shears said tissue against said female die.

10. The instrument of claim 7 further containing actuation means for bringing said rings into proximity, piercing the tissue, locking the rings and then cutting the excess tissue.

11. The instrument of claim 10 wherein said anvil and driving means are removable through the center of said rings such that said rings maintain proximated tissue therein upon the retraction of said instrument.

12. An instrument for anastomotic tissue fastening comprising:
   an anvil capable of holding a first absorbable staple ring;
   a driving mechanism capable of holding a second absorbable staple ring which mates and locks with said first absorbable staple ring, said driving mechanism capable of placing said rings into proximity of each other;
   knife means for cutting tissue, said knife means held within said driving mechanism; and
   first and second absorbable staple rings, wherein one of said absorbable staple rings contains a plurality of tissue piercing prongs arranged circumferentially about said ring for insertion through tissue and the other of said absorbable staple rings contains a plurality of receptors capable of locking said prongs therein with tissue placed between said rings on said prongs, said receptor shaped to engage said prongs so that each said prong is separated by at least a portion of a said receptor, and wherein said knife means are capable of cutting excess tissue contained inside the circumferences of said absorbable staple rings and being pulled through the joined staple rings, and wherein said prongs contain detent means and said receptors contain locking means for locking said receptors when said driving means bring said rings into proximity of each other; and
   wherein said die is a male die and said driving means further contains a spring such that said spring causes said rings to lock together by holding said rings against one another, and after said locking takes place, said knife means shears the tissue against said male die.

13. An instrument for anastomosic tissue fastening comprising:
   an anvil capable of holding a first absorbable staple plate;
   driving means capable of holding a second absorbable staple plate which self-aligns and locks with said first plate, said driving means capable of placing said plates into proximity of each other;
   knife means for cutting tissue, said knife means held within said driving means; and
   first and second absorbable staple plates wherein one of said plates contains a plurality of tissue piercing prongs arranged circumferentially about said plate for insertion through tissue and the other of said plate contains a plurality of receptors capable of locking said prongs therein with tissue placed between said plates and on said prongs, said receptor shaped to engage said prongs so that each said prong is separated by at least a portion of a said receptor and wherein said knife means are capable of cutting excess tissue held between said plates and wherein said prongs contain detent means and said receptors contain locking means for locking said receptors when said driving means being said plates into proximity of each other and wherein said plates are circular in shape, and said prongs and receptors are positioned on the circumferences of said plates, such that said plates are frangible inside said circumferences.

14. The instrument of claim 13 wherein said anvil further contains a die into which said knife means are actual, said knife means exerting a shear force on said tissue against said die.

15. The instrument of claim 14 wherein said die is a female die and said knife shears said tissue against said female die.

16. The instrument of claim 13 wherein said die is a male die and said driving means further contains a spring such that said spring causes said rings to lock together by holding said plates against one another, and after said locking takes place, said knife means shears the tissue against said male die.

17. The instrument of claim 13 further containing actuation means for bringing said plates into proximity, piecing the tissue, locking the plates and then cutting the excess tissue.

18. The instrument of claim 17 wherein said anvil and driving means are removable through the center of said rings such that said rings maintain proximated tissue therein upon the retraction of said instrument.

19. The instrument of claim 18 wherein upon breaking said piercing plate, said prongs are contained on a ring on said circumference and such that upon breaking said receiving plate, said receptors are contained on a ring on said circumference.

20. The instrument of claim 19 wherein said anvil further contains a die into which said knife means are actual, said knife means exerting a shear force on said tissue against said die.

21. The instrument of claim 20 wherein said prongs are sharpened to readily pierce tissue.

22. The instrument of claim 21 wherein said prongs contain detent means and said receptors contain latch means such that said detent means locks on said latch means.

23. The instrument of claim 20 wherein said plates are generally flat.

24. The instrument of claim 20 wherein each of said plates are frangible along a weakened portion of said plate, each said weakened portion comprising a ring of reduced thickness located on said plate and capable of breaking upon the exertion of a shear force along said plate.

25. The instrument of claim 24 wherein said die is a male die and said driving means further contain a spring such that said spring causes said plates to lock together by holding said plates against one another, and after said locking takes place, said knife means shears the tissue and the weakened portion of said plates against the male die.

26. The instrument of claim 24 wherein said die is a female die and said knife shears said tissue and the weakened portion of said plates against the female die.

27. The instrument of claim 24 further containing actuation means for bring said plates into proximity, piercing the tissue, locking said plates and then cutting the excess tissue and the weakened portion of said plates 28. The instrument of claim 27 wherein said anvil and driving means are removable through the center of said rings such that said rings maintain proximated tissue therein upon the retraction of said instrument.

29. A stapler comprising:
   a head portion having a circular cross section;
   a driving mechanism, said driving mechanism connected by a longitudinal shaft to said head portion;
   an anvil portion, said anvil portion connectable to said head portion and having a circular cross section smaller in diameter than said head portion; and
   fastener means inserted between said head portion and said anvil portion;
   wherein said fastener means are circular and frangible circumferentially into an outer and inner portion and said anvil portion fits through the outer circumference portion of said fastener means.

30. A method of stapling tissue together comprising:
   clamping tissue between an anvil of a surgical stapling apparatus and a head portion of a surgical stapling apparatus;
   driving a circular tissue-piercing ring containing a circumferentially arranged plurality of tissue-piercing prongs through said tissue;
   attaching said circular tissue-piercing ring to a circular receiving ring containing a plurality of receptors capable of locking said prongs therein;
   severing the claimed tissued on a circular knife held within the head portion of the apparatus;
   severing a circular portion of one of said tissue piercing ring or said receiving ring while severing said tissue, said circular portion having a smaller radial length than that of said tissue piercing prongs; and
   pulling the stapling anvil apparatus through the stapled together tissue.

* * * * *